United States Patent [19]
Guiolet et al.

[11] Patent Number: 5,636,637
[45] Date of Patent: Jun. 10, 1997

[54] METHOD FOR DETERMINING QUANTITIES CHARACTERISTIC OF THE BEHAVIOR OF A SURFACE, IN PARTICULAR OF THE HUMAN SKIN, SUBJECTED TO LIGHT RADIATION, AND APPARATUS FOR IMPLEMENTATION THEREOF

[75] Inventors: Alain Guiolet, Paris; Jean de Rigal, Gressy; Jean-Luc Leveque, Le Raincy, all of France

[73] Assignee: L'Oreal, Paris, France

[21] Appl. No.: 443,001

[22] Filed: May 17, 1995

[30] Foreign Application Priority Data

May 20, 1994 [FR] France ................................. 94 06187

[51] Int. Cl.⁶ ................................................. A61B 6/00
[52] U.S. Cl. .................................................... 128/665
[58] Field of Search .......................................... 128/665

[56] References Cited

U.S. PATENT DOCUMENTS

| | | | |
|---|---|---|---|
| 2,437,916 | 3/1948 | Greenwald | 128/665 |
| 4,398,541 | 8/1983 | Pugliese | 128/665 |
| 4,905,702 | 3/1990 | Foss | 128/665 |
| 5,198,875 | 3/1993 | Brazin et al. | |
| 5,363,854 | 11/1994 | Martens et al. | 128/665 |

FOREIGN PATENT DOCUMENTS

| | | |
|---|---|---|
| 0475803 | 3/1992 | European Pat. Off. . |
| 2650890 | 2/1991 | France . |
| 2651112 | 3/1991 | France . |
| 3827457 | 6/1989 | Germany . |
| 2235767 | 3/1991 | United Kingdom . |

*Primary Examiner*—William E. Kamm
*Attorney, Agent, or Firm*—Oliff & Berridge

[57] ABSTRACT

A method and apparatus determine quantities characteristic of the behavior of a surface, in particular, the human skin, subjected to light radiation. The apparatus includes an illumination device, a measurement detection device and a computation device. The apparatus and method determine a scattering spectrum, and calculate one or more quantities characteristic of the surface in a predetermined range of wavelengths.

22 Claims, 6 Drawing Sheets

METHOD FOR DETERMINING QUANTITIES CHARACTERISTIC OF THE BEHAVIOR OF A SURFACE, IN PARTICULAR OF THE HUMAN SKIN, SUBJECTED TO LIGHT RADIATION, AND APPARATUS FOR IMPLEMENTATION THEREOF

The present invention relates to a method for determining quantities characteristic of the behaviour of a surface, in particular of the human skin, subjected to light radiation, and an apparatus for implementation thereof.

Studying the behaviour of the skin with respect to light radiation is of great interest, in particular for researching new cosmetic products, in particular for sun protection, and for determining the sensitivity of various skin types to exposure to the sun.

As regards sun products, a scale called the protection factor scale is known which is supposed to quantify the protection efficiency of the various sun products which can be applied to the skin.

The method for determining these protection factors is based on clinical determinations which cannot have more than relative reliability.

The in vivo methods used to date also have relative reliability, mainly for the following two reasons:

On the one hand, the parameter traditionally used for calculating the protection factor is the overall light energy collected on illuminated skin, without distinguishing between the different types of light energy which may come from this surface.

On the other hand, the most recent sun products combine both chemical and physical phenomena of absorption, conversion and reflection of light, whereas the usual methods are unusable in view of the complexity of such phenomena.

With regard to methods for determining the tolerance of skin to exposure to the sun, they consist in exposing a small surface of the skin and in observing, over a period of approximately 24 hours, the erythemal reaction of the exposed region.

By carrying out successive tests, the threshold above which the self-protection mechanism of the skin, which is characterized by tanning amongst other things, becomes insufficient is determined. The exposed skin then undergoes burning which manifests itself in sunstroke.

The object of the present invention is to provide a method and an apparatus which make it possible, with a high degree of reliability, to characterize the behaviour of a surface such as the human skin with respect to light radiation and, consequently, the protection efficiency of sun products which can be applied to this surface.

In general, the method according to the invention is characterized by the following steps:

a predetermined region of a surface is illuminated with a polarized light beam oriented along an incidence direction which makes, with the normal to the said surface, an angle of between 10° and 50°, and preferably close to 35°, a scattering light signal originating from the illuminated region and oriented along the normal to the illuminated surface is recovered by filtering the collected signal through a polarizer whose polarization direction is perpendicular to the polarization direction of the incident signal, a scattering spectrum is obtained by sweeping a predetermined range of wavelengths of the incident signal, and measuring a collected on the basis of this scattering spectrum, optionally combined with supplementary measurements, one or more quantities characteristic of the optical behaviour of the illuminated surface in the predetermined range of wavelengths are calculated.

This method essentially relies on the fact that the characteristic quantity or quantities calculated are obtained by taking into account the scattering energy emitted by the illuminated surface.

This scattering energy is in fact of essential importance in so far as it accounts for the phenomena of absorption, fluorescence, reflection and diffraction which occur in any semi-transparent medium, in particular in the epidermis and in the dermis of the skin.

Up to this point, known measurement methods have been restricted either to characterizing the behaviour of the surface of the skin, independently of its pigmentation, or to overall measurement of diffuse reflection.

In order to increase the penetration of the light ray into the epidermis and the dermis, the orientation of the polarization of the incident light signal is preferably chosen to be parallel to the incidence plane.

According to a first embodiment of the invention, the following supplementary measurements are carried out:

a second, specular light signal originating from the illuminated region is recovered along a direction which is symmetrical to the incidence direction with respect to the normal to the illuminated surface, by filtering the collected signal through a polarizer whose polarization direction is parallel to the polarization direction of the incident signal, a specular spectrum is obtained by sweeping a predetermined range of wavelengths of the incident signal, and a pseudo-luminance spectrum is determined by sampling the scattering spectrum and the specular spectrum and by calculating, for each interval of this sampling, the ratio between the specular signal and the scattering signal, this pseudo-luminance spectrum being characteristic of the optical behaviour of the illuminated surface in the predetermined range of wavelengths.

This method may, in particular, be employed to characterize the protection efficiency of a sun product.

For this purpose, the above-described method is carried out a first time on a region of bare skin and this method is repeated on the same region of skin after the latter has been covered with a film of the sun product being studied, and the two pseudo-luminance spectra thus obtained are then compared in order to deduce therefrom, for each interval i in the sampling, a pseudo-luminance variance $DB_i$, and the following quantity is calculated:

$$I = \sum_i \alpha_i DB_i K_i$$

this value I being characteristic of the protection efficiency of the product, $\alpha_i$ being the erythemal efficiency coefficient in the interval in question, $K_i$ being the simulation weighting of the exposure system used.

The parameters $\alpha_i$ and $K_i$ are well known to the person skilled in the art and are available in specialist literature. By way of example, reference may be made, for example, to the article "A comparison of in vivo and in vitro testing of sunscreens formula" in Photochem and Photobiol, 1978, Vol. 29 pp. 559–566 (R. Sayres) or to the publication "SPF test methods", January 1994 by COLIPA.

The factor thus obtained can be compared with the protection factor which is assigned to sun products currently on the market.

According to a second embodiment of the method according to the invention, the following calculation is carried out:

$$ERD = \sum_i \alpha_i ED_i K_i$$

where $ED_i$ is the signal measured in the scattering spectrum for an interval i of the sampling, $\alpha_i$ and $K_i$ being respectively the erythemal efficiency coefficients and the weightings of the simulated exposure system.

The quantity ERD thus calculated characterizes the capacity of the skin to withstand exposure in the range of wavelengths in question, being inversely proportional to its tolerance.

The advantage of this second embodiment resides in the fact that it almost instantly provides an indication of the capacity of the skin to withstand exposure to the sun, which requires between 24 and 28 hours of experiment if the traditional method for determining the minimum erythema dose is employed.

This method furthermore has the advantage of not subjecting the skin of the test subject to exposure which, in the long term, might lead to irreversible sequelae.

A further subject of the present invention is an apparatus for determining quantities characteristic of the behaviour of a surface, in particular the human skin, subjected to light radiation.

This apparatus is characterized in that it comprises a head which is applied against a surface, a light source which can send a light beam onto a region of the surface, a polarizer placed between the light source and the illuminated region of the skin, the polarized light beam forming, with the normal to the illuminated surface, an angle of between 10° and 50°, and preferably close to 35°, a light-signal detector oriented so as to collect the light signal originating from the illuminated region along the normal to the illuminated surface, a polarizer whose polarization direction is perpendicular to the polarization direction of the incident signal and which is placed between the illuminated surface and the said light-signal detector, means for recording, by sweeping a predetermined range of wavelengths of the incident signal, a scattering spectrum obtained by measuring the light signal collected by the detector, and computation means for calculating, on the basis of the said scattering spectrum, one or more quantities which are characteristic of the optical behaviour of the illuminated surface in the predetermined range of wavelengths in question.

In a preferred embodiment of the invention, the first polarizer placed between the light source and the illuminated surface is oriented so that the polarization direction of the incident beam is parallel to the incidence plane.

In a particular embodiment of the invention, the light source is connected to the applicator head of the apparatus via an optical fibre, and the light-signal detector is also connected to the applicator head of the apparatus by an optical fibre, the applicator head of the apparatus supporting the first and second polarizers.

In a preferred embodiment of the invention, the applicator head comprises reference means which make it possible to apply it onto a surface of skin while always maintaining the same incidence plane.

According to a preferred variant of this embodiment, the apparatus comprises for this purpose a mask which can be applied directly onto the skin, this mask comprising a masking element provided with an orifice of, for example, square shape, while the applicator head comprises a part of the same shape which is capable of cooperating with the mask when the apparatus is applied onto the surface of the skin, and adhesive supports to which the masking element is connected by removable fastening means.

The adhesive supports thus remain permanently on the skin, in the vicinity of the surface in question, while the masking element can be applied or withdrawn as desired, by virtue of the removable fastening means.

In this embodiment, the apparatus is always applied to the skin by means of the mask with which it cooperates.

During each measurement, it is sufficient to fix the mask to the adhesive support and apply the apparatus according to the invention by making its applicator head cooperate with the orifice in the mask.

In order better to explain the invention, a description will now be given of embodiments, given by way of non-limiting examples, with reference to the attached drawing, in which.

Figure 1:
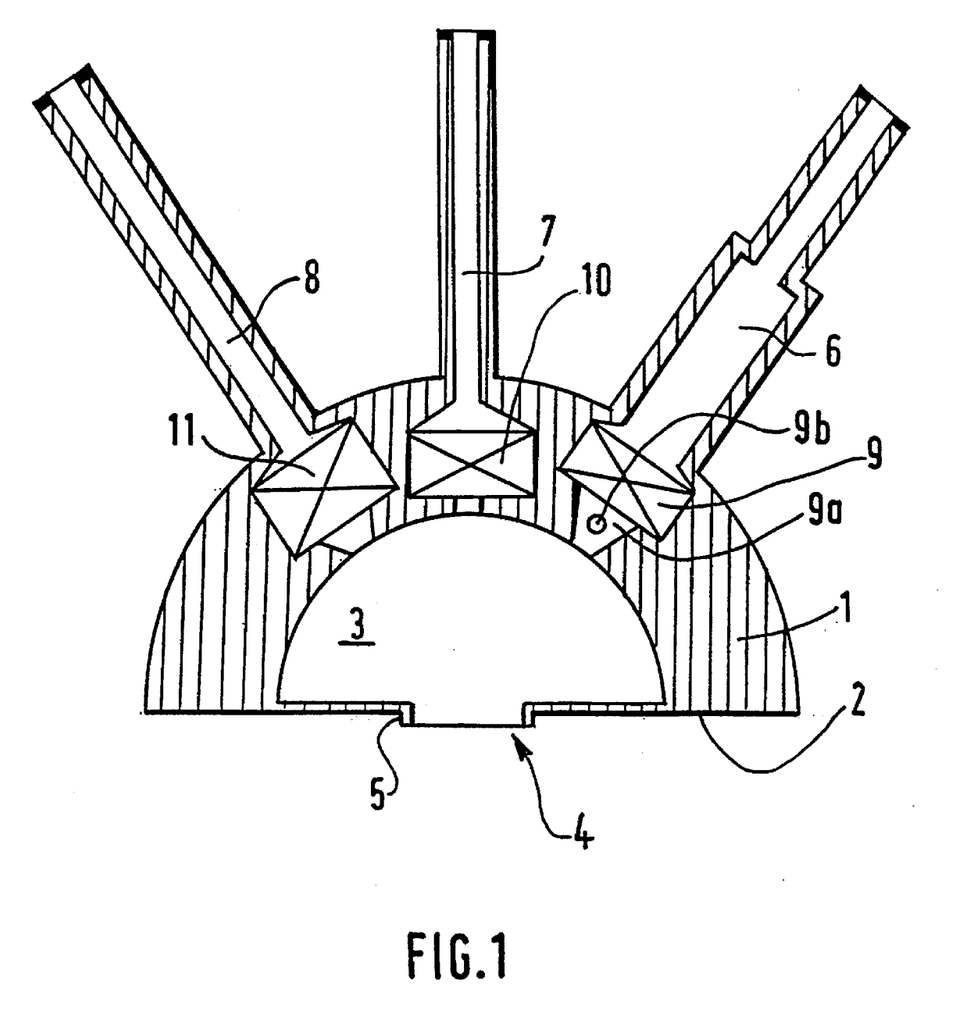
FIG. 1 is an axial section of an apparatus according to one embodiment of the invention.
Figure 2:
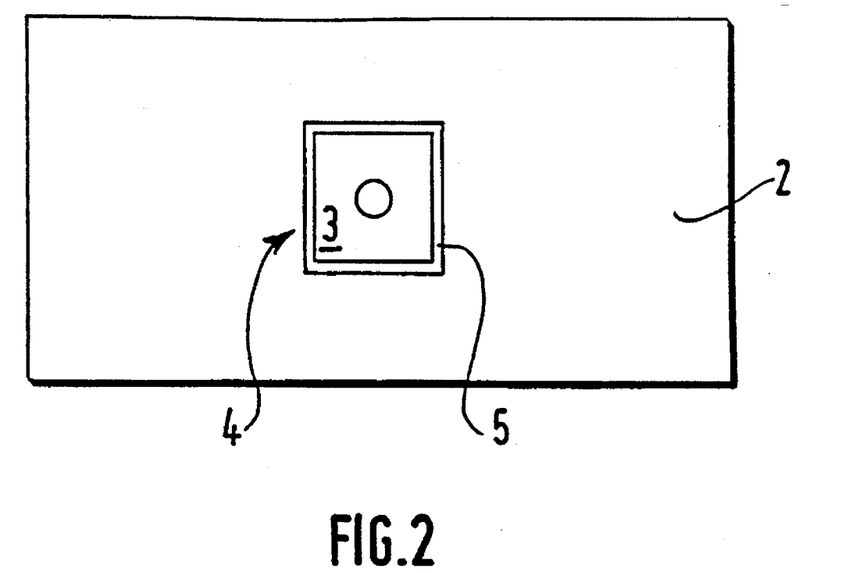
FIG. 2 is a bottom view of the apparatus in FIG. 1.
Figure 3:
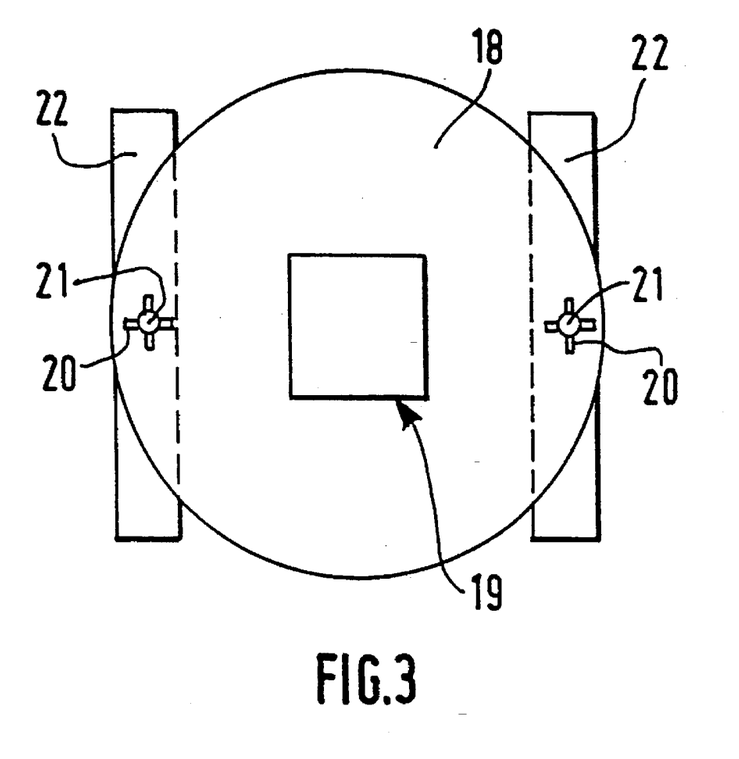
FIG. 3 is a plan view of an orientation mask according to one embodiment of the invention.

The apparatus represented in FIGS. 1 to 3 is in the form of a hemicylindrical casing 1 resting on its diametral plane 2.

The internal cavity 3 of the casing 1 constitutes an illumination chamber.

This chamber 3 opens onto the casing 1 via a square orifice 4, the edges 5 of which project out of the casing beyond its diametral plane 2.

In its part opposite the plane 2, the casing 1 comprises three channels 6, 7 and 8, the directions of which converge substantially towards the centre of the orifice 4.

The direction of the channel 7 is normal to the diametral plane 2, while the directions of the channels 6 and 8 form an angle of approximately 35° with the direction of the channel 7.

Each of the channels 6, 7 and 8 open into the illumination chamber 3 through a polarizer 9, 10, 11.

The mouth of each channel is designed to receive the end of an optical fibre.

The channel 6 is intended to convey, into the illumination chamber 3, a preferably parallel incident light beam which illuminates a substantially ovoid region located in line with the orifice 4 of a surface, not shown, against which the apparatus is applied via its diametral plane 2.

The polarizer 9 polarizes the incident beam preferably parallel to the incidence plane which corresponds to the plane of FIG. 1.

The channel 7 collects, by virtue of the polarizer 10, the light energy originating from the illuminated surface, which is polarized perpendicularly to the incidence plane.

The channel 7 thus collects only the light signal scattered by the illuminated surface and not the reflected signal, which is polarized parallel to the incidence plane like the incident beam.

The channel 8 collects, by virtue of the polarizer 11, the specular light energy polarized in the incidence plane. This energy corresponds to the energy reflected by the illuminated surface.

Figure 4:
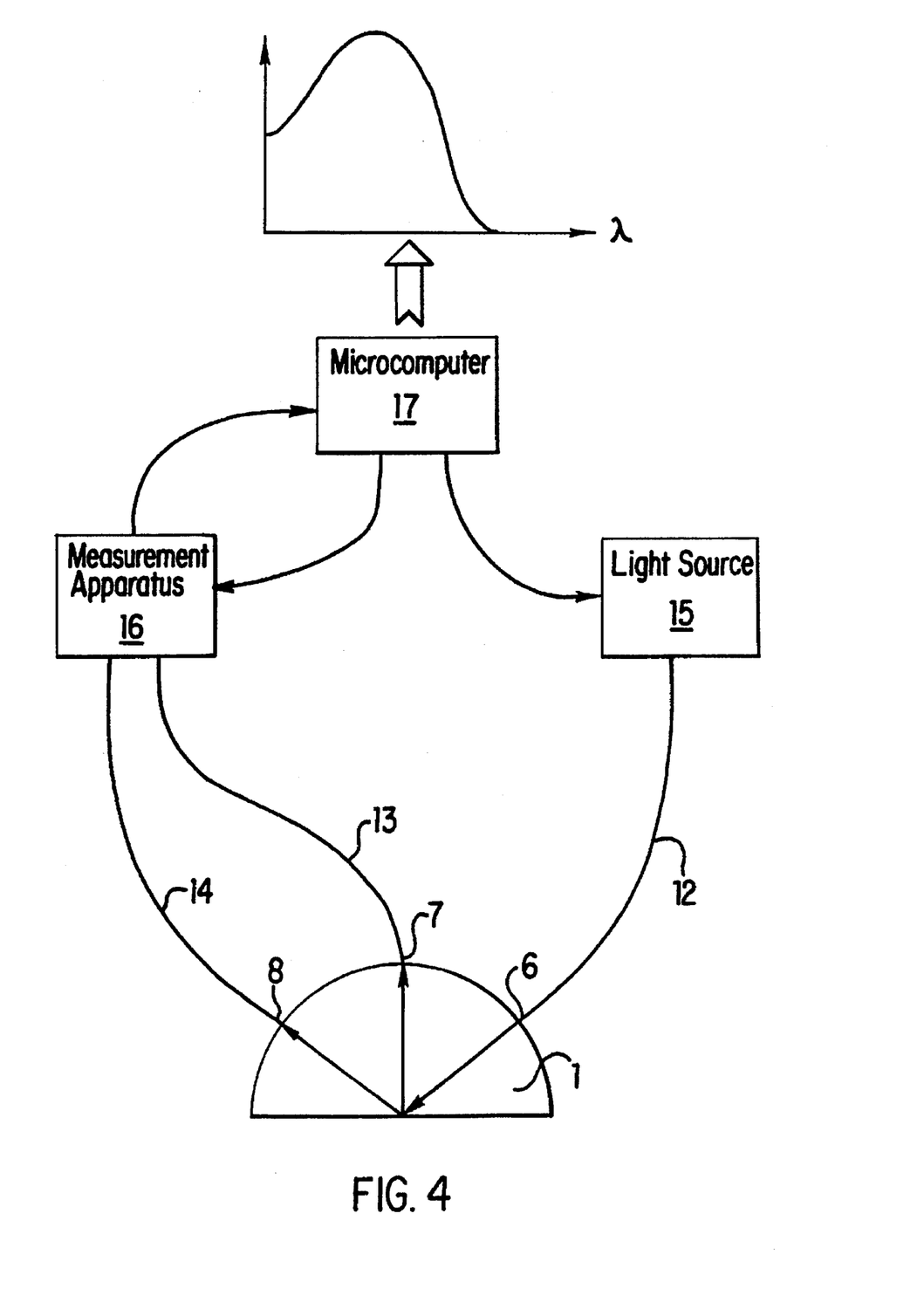
FIG. 4 is a block diagram of the various elements forming the apparatus according to the invention.

In FIG. 4, the apparatus according to the invention is connected to optical fibres 12, 13 and 14 which convey the incident, scattered and specular light signals, respectively, which pass through the channels 6, 7 and 8.

The optical fibre 12 is connected to a light source 15, for example a xenon lamp combined with a monochromater, while the optical fibres 13 and 14 are connected to a measurement apparatus 16 consisting, for example, of two photomultipliers and a multichannel digital volt meter.

A microcomputer 17 controls the light source 15 and the measurement apparatus 16 and collects the measurements taken.

On the basis of this information, the microcomputer 17 establishes a pseudo-luminance spectrum as will be explained with reference to FIGS. 5a, 5b and 5c.

In order to apply it to the skin of a test subject, the apparatus illustrated is advantageously combined with the mask which is represented in FIG. 3.

This mask comprises a masking disc 18 which is provided in its central part with an orifice 19 whose dimensions correspond to those of the orifice 4 made in the diametral plane of the casing 1.

The masking disc 18 comprises two diametrically opposite cross-shaped passages 20 intended for rivet heads 21 which are solidly attached to adhesive tapes 22.

The adhesive tapes 22 are intended to be adhesively bonded onto the skin of the test subject, on either side of the region of skin to be studied.

These adhesive tapes 22 thus remain adhesively bonded throughout the measurement session, whereas the masking disc 18 can easily be removed.

In this way, the region to be studied can be prepared without being hampered by the masking disc 18.

Each time a measurement is taken, the masking disc 18 is fixed onto the adhesive tapes 22 by means of the rivet heads 21. The region under study is thus perfectly defined by the square orifice 19.

The apparatus is then applied against the masking disc 18 by making the edges 5 of the orifice 4 penetrate into the orifice 19 in the masking disc.

Between taking measurements, the masking disc 18 can be withdrawn in order to apply a treatment to the skin surface being studied.

By virtue of the square shape of the cooperating orifices 4 and 19, the apparatus is always oriented in the same direction when taking measurements, which makes it possible to take comparative measurements in succession, while maintaining the same illumination conditions of the surface of the skin.

In fact, in view of the surface structure of the skin, a variation in orientation of the incidence plane might result in vitiation of the measurements and prevent any significant comparison.

Of course, the square shape of the orifices 4 and 19 may be replaced by any non-circular shape which makes it possible to recover the preferential orientation of the incidence plane.

With references to FIGS. 5a, 5b and 5c, an explanation will now be given of how the microcomputer 17 establishes the pseudo-luminance spectrum according to the invention.

On the basis of the signals originating from the channels 7 and 8, the microcomputer establishes the scattering spectrum and the specular spectrum, respectively, of the surface studied, by sweeping the wavelengths of the incident light beam through a predetermined wavelength range.

In the present case, the monochromater of the light source 15 is controlled by the microcomputer 17, as illustrated in FIG. 4, in order, for example, to scan a range of wavelengths of from 275 to 400 nm.

Each specular and scattering spectrum is then sampled at small intervals, for example of 5 nanometres.

For each interval, the ratio between the specular energy collected in the channel 8 and the scattering energy collected in the channel 7 is calculated.

This ratio defines the pseudo-luminance according to the present invention.

Figure 5A:
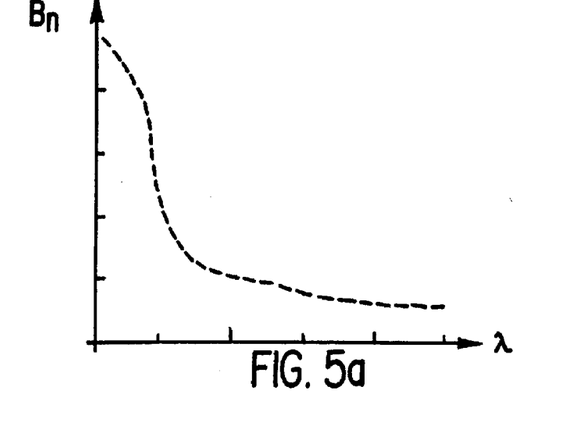
FIGS. 5a and 5b are diagrams each representing one pseudo-luminance spectrum on bare skin and on bare skin covered with a protection product, respectively.
Figure 5B:
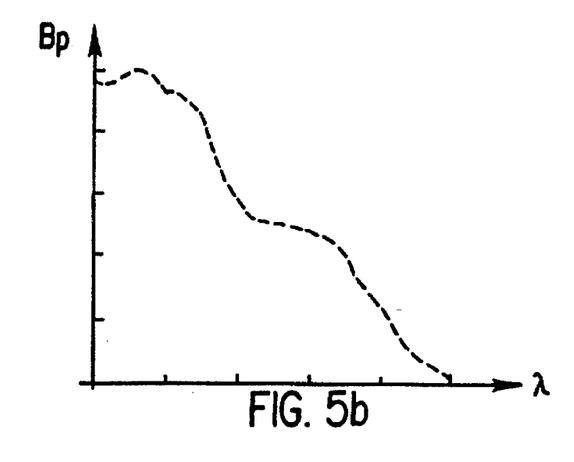

Such a pseudo-luminance spectrum Bn is represented in FIG. 5a, which corresponds to a measurement carried out on bare skin, and in FIG. 5b which corresponds to a pseudo-luminance spectrum Bp collected on the same skin, 15 min after application of a sun product in a quantity of 1 mg/cm².

Figure 5C:
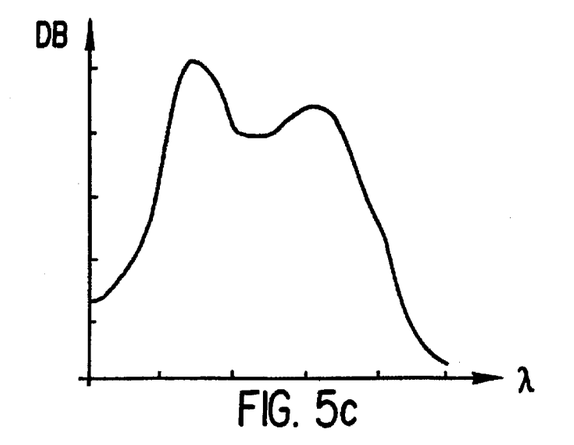
FIG. 5c is a diagram representing a pseudo-luminance variation spectrum of this product.

On the basis of these two spectra, it is possible according to the invention to establish the pseudo-luminance variation spectrum DB which is represented in FIG. 5c. This spectrum characterizes the behaviour of the product with respect to light.

This spectrum is obtained by calculating, for each interval i:

$$DB_i = \frac{Bp(i) - Bn(i)}{Bn(i)}$$

where Bp(i) is the value of the pseudo-luminance in the interval i on bare skin and Bn(i) is the value of the pseudo-luminance on the skin covered with the product in the wavelength interval i.

This pseudo-luminance variation spectrum makes it possible, for example, to characterize the protection efficiency of the sun product in question.

Figure 6:
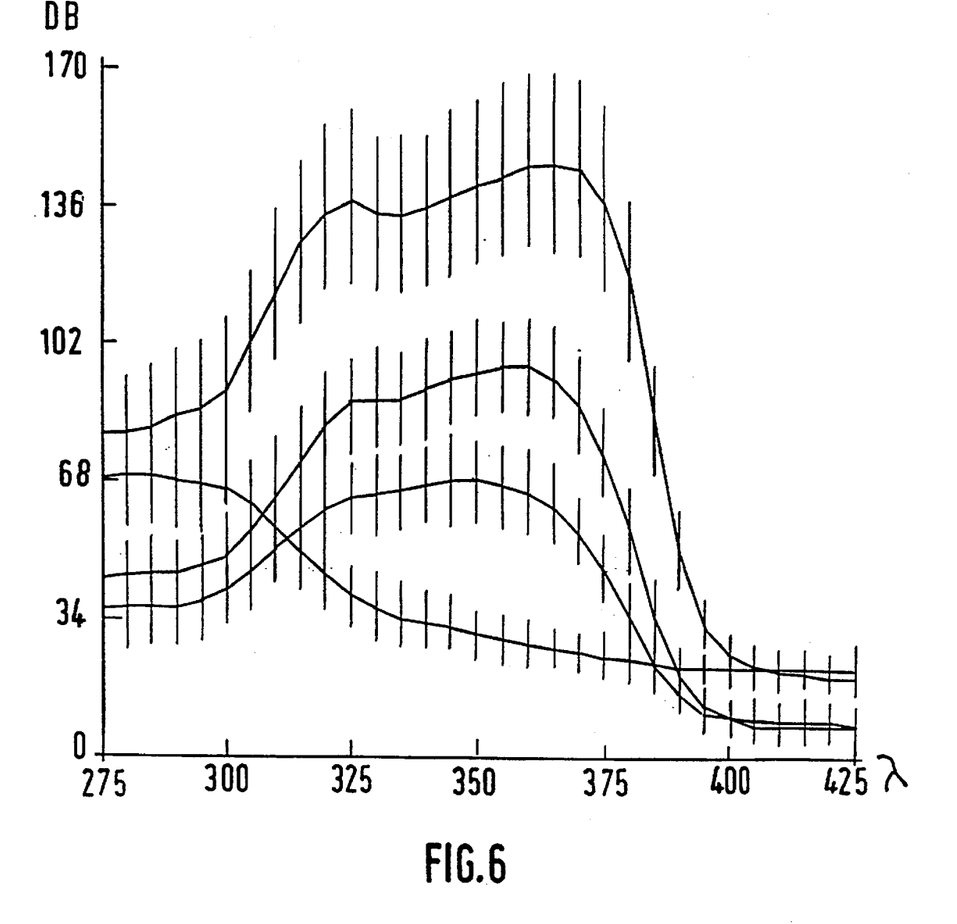
FIG. 6 is a diagram representing the pseudo-luminance variation spectra of various sun protection products.

FIG. 6 represents curves of pseudo-luminance variation as a function of wavelength for 4 sun products with different protection factors.

The four products A, B, C, D considered have the following composition:

| Products | vehicle | PARSOL 1789 (from the company Givaudan) | MEXORIL SX (from the company L'OREAL) |
| --- | --- | --- | --- |
| A | YES | 0% | 0% |
| B | YES | 0.5% | 1% |
| C | YES | 1% | 2% |
| D | YES | 2% | 4% |

The product A is a placebo, and its pseudo-luminance variation curve expresses only the absorption of light by the elements of the formula of the placebo.

The other three products B, C, D exhibit a pseudo-luminance variation curve whose maximum is reached for a wavelength of approximately 350 nanometres.

This maximum validates the relevance of the pseudo-luminance variation curve defined according to the invention, because it is moreover known that the maximum in the absorption spectrum of the three products tested lies between 350 and 355 nanometres.

On the basis of the pseudo-luminance variation curves in FIG. 6, it is possible to calculate a factor for each tested product B, C, D which is characteristic of the protection efficiency of the product, according to the following formula:

$$I = \sum_i \alpha_i DB_i K_i$$

where $\alpha_i$ is the erythemal efficiency coefficient at the wavelength of the interval in question, and
$K_i$ is the weighting of the simulated exposure system.

Two sums are calculated separately. One for wavelengths covering the UVA range, that is to say between 320 and 400 nanometres, and the other for wavelengths corresponding to UVB, that is to say 280 to 320 nanometres.

A third sum can be calculated over the entire spectrum, that is to say between 280 and 400 nm.

The protection efficiency factors obtained are summarized in the following table:

|  | B | C | D |
| --- | --- | --- | --- |
| UVA | 60 | 87 | 131 |
| UVB | 120 | 175 | 217 |

These factors are remarkably correlated with the conventional protection factors of the products B, C, D tested.

Employing this formula for determining the efficiency of a product therefore makes it possible to calculate a protection efficiency factor for new products and to do this directly on the skin of a test subject. In this way, various protection efficiency factors can be determined as a function of the skin type of the test subject.

In particular, it is possible to determine protection efficiency factor scales which are, for example, suited to fair or olive skin types.

On the basis of the scattering spectrum established by the microcomputer 17, it is also possible, according to the invention, to determine a quantity characteristic of the self-protection capacity of a skin.

For this purpose, starting with the scattering spectrum ED, the back-scattered energy ERD is calculated by the following formula $$ERD = \sum_i \alpha_i ED_i K_i$$

in which $\alpha_i$ and $K_i$ are defined as explained hereinabove, and $ED_i$ is the scattering energy in the wavelength interval i in question.

In order to take into account imperfections of the light source and to overcome the errors thus created, which might disrupt the measurements, it is possible also to collect a part of the incident beam and correct each term $ED_i$ by a coefficient $L_i$ characteristic of the energy emitted by the incident beam in the wavelength corresponding to the interval i.

In this case, the back-scattered energy is defined by the following formula:

$$ERD = \sum_i \alpha_i ED_i L_i K_i$$

In order to collect a part of the incident beam, on the apparatus represented in FIG. 1, it is possible to place a conical mirror 9a at the output of the polarizer 9, and deflect a part of the incident beam towards an orifice 9b, at the mouth of which measurement and computation means make it possible to determine the coefficients $L_i$.

Figure 7:
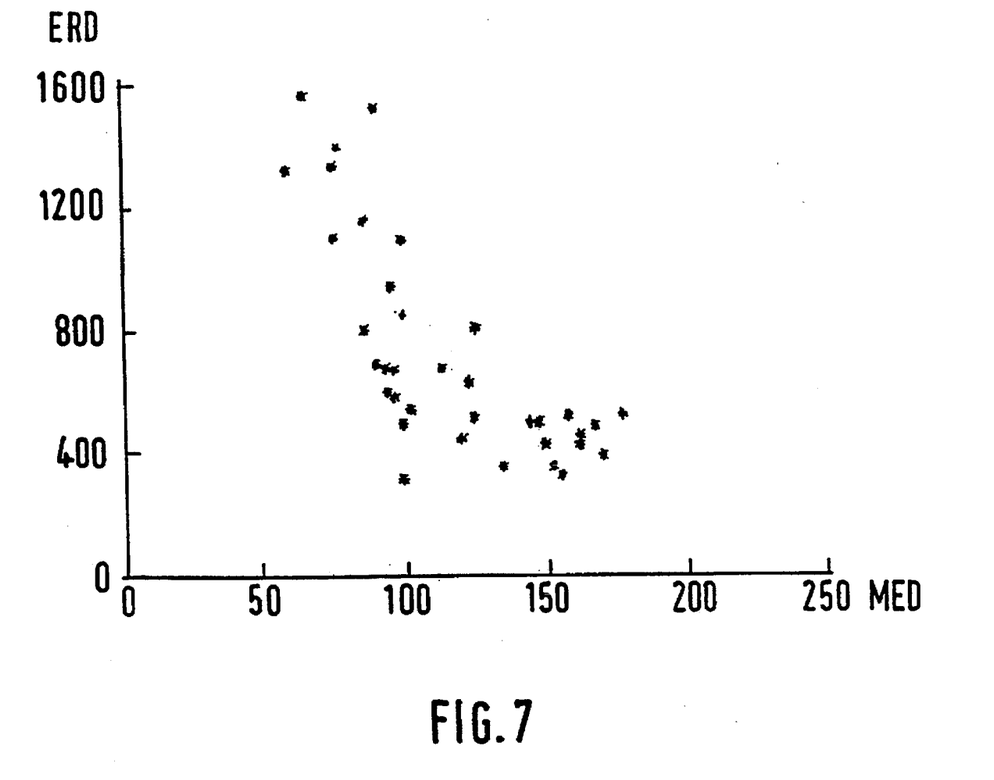
FIG. 7 is a diagram showing the correlation between the back-scattered energy ERD, in the context of the invention, and the minimum erythema dose of a skin.

The calculated values of the ERD, obtained from experiments carried out on the backs of a plurality of test subjects, whose minimum erythema doses varied from 60 to 182 mJ/cm$^2$, are plotted in FIG. 7.

It will be recalled that the minimum erythema dose is defined as being the maximum energy which a skin can withstand before triggering a solar erythema.

This minimum erythema dose is measured by a standard method which consists in exposing a skin and in observing the reaction of this skin after 24 hours.

In FIG. 7 it is clearly seen that the back-scattered energy ERD is inversely proportional to the minimum erythema dose MED.

The method for determining the back-scattered energy ERD according to the invention thus makes it possible a priori to assess the self-protection capacity of a skin and to do this almost instantaneously, without it being necessary to expose this skin and to wait approximately 24 hours.

It is clear that the embodiments which have just been described imply no limitation and that any desirable modifications may be made to them without thereby departing from the scope of the invention.

In particular, the apparatus which has been described comprises a monochromatic light source and photomultipliers associated with a multichannel digital volt meter. However, it would also be possible to use a white light source and CCD type detectors, in which case the energy spectra would be measured instantaneously, without the microcomputer needing to act on the light source.

Furthermore, the method and the apparatus according to the invention can be used to characterize the behaviour in response to light of cosmetic products applied to the skin, in particular make-up products.

I claim:

1. A method for determining quantities characteristic of the behavior of a surface subjected to light radiation, comprising:

illuminating a predetermined region of a surface with a polarized light beam oriented along an incidence direction which makes, with the normal to the surface, an angle of between 20° and 50°;

recovering a scattering light signal originating from the predetermined region and oriented along the normal to the surface by filtering the scattering light signal through a polarizer whose polarization direction is perpendicular to the polarization direction of the light beam;

obtaining a scattering spectrum by measuring the scattering light signal and by sweeping a predetermined range of wavelengths of the polarized light beam; and calculating on the basis of the scattering spectrum, at least one quantity characteristic of an optical behavior of the surface in the predetermined range of wavelengths.

2. The method according to claim 1, wherein the orientation of polarization of the light beam is parallel to an incidence plane, said incidence plane being defined by said incidence direction and said normal to the surface.

3. The method according to claim 2, further comprising:

recovering a second, specular light signal originating from the predetermined region along a direction which is symmetrical to the incidence direction of the light beam with respect to the normal to the surface by filtering a collected signal through a polarizer whose polarization direction is parallel to the polarization direction of the light beam;

obtaining a specular spectrum by measuring the second, specular light signal and by sweeping a predetermined range of wavelengths of the light beam;

determining a pseudo-luminance spectrum by sampling the scattering spectrum and the specular spectrum; and calculating, for each interval of the sampling, a ratio between the specular signal and the scattering signal, wherein the pseudo-luminance spectrum is characteristic of an optical behavior of the surface in the predetermined range of wavelengths.

4. The method according to claim 3, wherein said predetermined region of a surface is a predetermined region of bare skin; and wherein said illuminating, recovering, obtaining and calculating steps are performed on the same region of bare skin before and after said bare skin has been covered with a film of a sun product, and the method further comprises:

comparing the two pseudo-luminance spectra;

obtaining for each interval i in the sampling, a pseudo-luminance variance $DB_i$; and calculating a value I characteristic of the protection efficiency of the product according to the following formula:

$$I = \sum_i \alpha_i DB_i K_i$$

where $\alpha_i$ is an erythemal efficiency coefficient in the interval in question, and $K_i$ is a weighting.

5. The method according to claim 2, further comprising determining back scattering energy ERD according to the following formula:

$$ERD = \sum_i \alpha_i ED_i K_i$$

where $ED_i$ is a signal measured in the scattering spectrum for an interval i of the sampling, $\alpha_i$ is an erythemal efficiency coefficient and $K_i$ is a simulation weighting.

6. The method according to claim 1, further comprising:

recovering a second, specular light signal originating from the predetermined region along a direction which is symmetrical to the incidence direction of the light beam with respect to the normal to the surface by filtering a collected signal through a polarizer whose polarization direction is parallel to the polarization direction of the light beam;

obtaining a specular spectrum by measuring the second, specular light signal and by sweeping a predetermined range of wavelengths of the light beam;

determining a pseudo-luminance spectrum by sampling the scattering spectrum and the specular spectrum; and calculating, for each interval of the sampling, a ratio between the specular signal and the scattering signal, wherein the pseudo-luminance spectrum is characteristic of an optical behavior of the surface in the predetermined range of wavelengths.

7. The method according to claim 6, wherein said predetermined region of a surface is a predetermined region of bare skin, and wherein said illuminating, recovering, obtaining and calculating steps are performed on the same region of bare skin before and after said bare skin has been covered with a film of a sun product; and the method further comprises:

comparing the two pseudo-luminance spectra;

obtaining for each interval i in the sampling, a pseudo-luminance variance $DB_i$; and calculating a value I characteristic of the protection efficiency of the product according to the following formula:

$$I = \sum_i \alpha_i DB_i K_i$$

where $\alpha_i$ is an erythemal efficiency coefficient in the interval in question, and $K_i$ is a weighting.

8. The method according to claim 1, further comprising determining back scattering energy ERD according to the following formula:

$$ERD = \sum_i \alpha_i ED_i K_i$$

where $ED_i$ is a signal measured in the scattering spectrum for an interval i of the sampling, $\alpha_i$ is an erythemal efficiency coefficient and $K_i$ is a simulation weighting.

9. The method according to claim 1, wherein the surface is human skin.

10. The method according to claim 1, wherein the polarized light beam is oriented along an incidence direction which makes, with the normal to the surface, an angle of approximately 35°.

11. An apparatus for determining qualities characteristic of behavior of a surface subjected to light radiation, the apparatus comprising:

an applicator head;

a light source connected to said applicator head, said light source being adapted to send an incident light beam onto a region of the surface;

a first polarizer positioned between the light source and the region, said first polarizer polarizing said light beam and the light beam forming, with the normal to the surface, an angle of between 10° and 50°;

a light-signal detector connected to said applicator head and oriented so as to collect light originating from the region along the normal to the surface;

a second polarizer whose polarization direction is perpendicular to the polarization direction of the light beam, said second polarizer being positioned between the region and said light-signal detector;

means for obtaining a scattering spectrum by sweeping a predetermined range of wavelengths of the light beam;

means for measuring the light collected by the detector; and computation means for calculating on the basis of the said scattering spectrum one or more quantities which are characteristic of optical behavior of the surface in a predetermined range of wavelengths.

12. The apparatus according to claim 11, wherein the first polarizer is positioned between the light source and the region and is oriented so that the polarization direction of the incident beam is parallel to an incidence plane, said incidence plane being defined by said incidence direction and said normal to the surface.

13. The apparatus according to claim 12, wherein the applicator head comprises reference means for orienting the applicator head.

14. The apparatus according to claim 13, wherein said reference means comprises a mask which can be applied directly onto the region, said mask comprising a masking element provided with an orifice of asymmetric shape; wherein said applicator head comprises a central part of the same shape as said orifice, said central part cooperating with said orifice when said apparatus is applied onto the region; and wherein adhesive supports are connected to said masking element by removable, fastening means.

15. The apparatus according to claim 14, wherein the orifice is square.

16. The apparatus according to claim 13, wherein the reference means make it possible to apply the applicator head onto a surface of skin while always maintaining the same incidence plane.

17. The apparatus according to claim 11, wherein the applicator head comprises reference means for orienting the applicator head.

18. The apparatus according to claim 17, wherein said reference means comprises a mask which can be applied directly onto the region, said mask comprising a masking element provided with an orifice of asymmetric shape; wherein said applicator head comprises a central part of the same shape as said orifice, said central part cooperating with said orifice when said apparatus is applied onto the region; and wherein adhesive supports are connected to said masking element by removable fastening means.

19. The apparatus according to claim 18, wherein the orifice is square.

20. The apparatus according to claim 17, wherein the reference means make it possible to apply the applicator head onto a surface of skin while always maintaining an incidence plane, said incidence plane being defined by said incidence direction and said normal to the surface.

21. The apparatus according to claim 11, wherein the surface is human skin.

22. The apparatus according to claim 11, wherein the light beam forms, with the normal to the surface, an angle of approximately 35°.

* * * * *